US012054517B2

(12) United States Patent
Takada et al.

(10) Patent No.: US 12,054,517 B2
(45) Date of Patent: Aug. 6, 2024

(54) MYELOID DIFFERENTIATION FACTOR 2 (MD2) SIGNALING AND MODULATION

(71) Applicant: The Regents of the University of California, Oakland, CA (US)

(72) Inventors: Yoshikazu Takada, Davis, CA (US); Yoko Takada, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 30 days.

(21) Appl. No.: 17/734,432

(22) Filed: May 2, 2022

(65) Prior Publication Data

US 2022/0356211 A1 Nov. 10, 2022

Related U.S. Application Data

(60) Provisional application No. 63/184,562, filed on May 5, 2021.

(51) Int. Cl.
  *C07K 14/00* (2006.01)
  *A61P 29/00* (2006.01)
  *C12N 15/63* (2006.01)

(52) U.S. Cl.
  CPC ............ *C07K 14/001* (2013.01); *A61P 29/00* (2018.01); *C12N 15/63* (2013.01); *C07K 2319/034* (2013.01)

(58) Field of Classification Search
  CPC  C07K 14/001; C07K 2319/034; C07K 14/47; A61P 29/00; C12N 15/63; G01N 2333/70557; G01N 33/566; G01N 2500/02; A61K 38/00
  See application file for complete search history.

(56) References Cited

PUBLICATIONS

Zhixia et al (WISP1-αvβ3 integrin signaling positively regulates TLR-triggered inflammation response in sepsis induced lung injury (Scientific Reports, 2016, vol. 6:28841 (Year: 2016).*

Zhixia et al Integrin β3 Modulates TLR4-Mediated Inflammation by Regulation of CD14 Expression in Macrophages in Septic Condition. Shock 53(3):p. 335-343, Mar. 2020. (Year: 2020).*
Aderem (Toll-like receptors in the induction of the innate immune response. Nature | vol. 406 | Aug. 17, 2000 (Year: 2000).*
Gerold et al., A Toll-like receptor 2-integrin b3 complex senses bacterial lipopeptides via vitronectin. Nat. Immunol., 2008, vol. 9(7): 761-768. (Year: 2008).*
Li et al., Novel Pure αVβ3 Integrin Antagonists That Do Not Induce Receptor Extension, Prime the Receptor, or Enhance Angiogenesis at Low Concentrations. ACS Pharmacol. Transl. Sci., 2019, vol. 2: 387-401. (Year: 2019).*
Monick et al., Interaction of matrix with integrin receptors is required for optimal LPS-induced MAP kinase activation. Am J Physiol Lung Cell Mol Physiol., 2002, vol. 283: L390-L302. (Year: 2002).*
Shuto et al., Membrane-anchored CD14 is required for LPS-induced TLR4 endocytosis in TLR4/MD-2/CD14 overexpressing CHO cells. Biochem. Biophys. Res. Commun., 2005, vol. 338: 1402-1409. (Year: 2005).*
Viriyakosol et al., MD-2 Binds to Bacterial Lipopolysaccharide*. The J. Biol. Chem., 2001, vol. 276(41): 38044-38051. (Year: 2001).*

* cited by examiner

*Primary Examiner* — Ganapathirama Raghu
(74) *Attorney, Agent, or Firm* — Kilpatrick Townsend & Stockton LLP

(57) ABSTRACT

The present invention resides in the discovery that the specific interaction between Myeloid Differentiation factor 2 (MD2) and integrin, especially integrin αvβ3, is involved in cellular signaling mediated by MD2-integrin, such as inflammatory response including sepsis. Thus, this invention provides for a novel method for inhibiting integrin signaling by using an inhibitor of MD2-integrin binding, such as a dominant negative mutant of MD2 without integrin-binding capability. A method for identifying inhibitors of MD2-integrin binding is also described. Further disclosed are polypeptides, nucleic acids, host cells, and corresponding compositions for inhibiting MD2-integrin signaling.

20 Claims, 2 Drawing Sheets
Specification includes a Sequence Listing.

MYELOID DIFFERENTIATION FACTOR 2 (MD2) SIGNALING AND MODULATION

RELATED APPLICATIONS

This application claims priority to U.S. Provisional Patent Application No. 63/184,562, filed May 5, 2021, the contents of which are incorporated by reference in the entirety for all purposes.

REFERENCE TO SUBMISSION OF A SEQUENCE LISTING AS A TEXT FILE

The Sequence Listing written in file 081906-1303532-242310US_SL.txt created on Jun. 29, 2022, 2,284 bytes, machine format IBM-PC, MS-Windows operating system, is hereby incorporated by reference in its entirety for all purposes.

BACKGROUND OF THE INVENTION

Myeloid Differentiation factor 2 (MD2) is a secretory protein that binds to lipopolysaccharide (LPS) and toll-like receptor 4 (TLR4) on the cell surface to form the LPS-MD2-TLR4 complex. This process is critically involved in TLR4 signaling from LPS. Previous studies showed that integrin $\alpha v\beta 3$ is involved in TLR4 signaling, since antagonists to integrin $\alpha v\beta 3$ block TLR4 signaling from LPS and that integrin $\alpha v\beta 3$ associates with TLR. The details of integrin $\alpha v\beta 3$-TLR4-MD2 interaction remains unclear, however. The present inventors have discovered that integrin $\alpha v\beta 3$ directly binds to MD2. Using docking simulation and mutagenesis techniques, they have identified amino acid residues of MD2 involved in integrin binding. MD2 mutants that are defective in integrin-binding have been generated and analyzed. Since integrin-MD2 interaction is critical for MD2 signaling, MD2 mutants defective in integrin-binding are defective in signaling and thus can act as antagonists. MD2-mediated signaling being a part of inflammatory response, MD2-integrin interaction is thus a potential target for modulating inflammatory responses and MD2 mutants can be used in controlling inflammation in therapeutic applications such as treating sepsis. Since inflammation is implicated in many diseases and disorders, there exists an urgent need for the development of new and effective therapeutics targeting inflammation and reducing or eliminating harmful outcomes from inflammation. The present invention fulfills this and other related needs.

BRIEF SUMMARY OF THE INVENTION

This invention provides new methods and compositions useful for inhibiting MD2 signaling in a cell, based on the discovery that the interaction between MD2 and certain integrin molecules is involved in MD2-mediated signaling. Thus, in one aspect, the present invention provides an isolated peptide comprising the amino acid sequence of SEQ ID NO:1 with at least one substitution at residues 20 and 39, and the peptide has decreased binding to integrin $\alpha v\beta 3$ compared with SEQ ID NO:1.

In some embodiments, the substitution in the peptide at residue 20 and/or 39 is an E substitution. In some embodiments, the substitution at residue 20 and/or 39 is not an A substitution. In some embodiments, the peptide comprises SEQ ID NO:1 with one E substitution at residue 20. In some embodiments, the peptide consists of SEQ ID NO:1 with one E substitution at residue 20. In some embodiments, the peptide comprises SEQ ID NO:1 with one E substitution at residue 39. In some embodiments, the peptide consists of SEQ ID NO:1 with one E substitution at residue 39. In some embodiments, the peptide comprises SEQ ID NO:1 with one E substitution at each of residues 20 and 39. In some embodiments, the peptide consists of SEQ ID NO:1 with one E substitution at each of residues 20 and 39. In some embodiments, the peptide is fused with one or more heterologous peptide sequence to form a longer fusion protein, for example, with one heterologous amino acid sequence located at either or both N-terminus and C-terminus. In some embodiments, the peptide is conjugated with a heterologous moiety such as a detectable moiety for easy detection, an affinity moiety for easy purification (e.g., 6×His (SEQ ID NO: 2) or glutathione S-transferase, GST), or a solid support. In some embodiments, the peptide or its fusion protein further comprises modification such as substitution with D-amino acid(s) or PEGylation (covalent attachment or amalgamation of polyethylene glycol (PEG) polymer chains) at one or more residues, which may be directly PEGylated or substituted with another amino acid such as Lys, which permits PEGylation. PEGylation can take place on amino acids including lysine, cysteine, histidine, arginine, aspartic acid, glutamic acid, serine, threonine, tyrosine. Further, the N-terminal amino group and the C-terminal carboxylic acid of the peptide or its fusion protein can also be used, directly or upon functionalization, as a site for PEGylation.

The second aspect of the present invention provides a nucleic acid comprising a polynucleotide sequence encoding the peptide or its fusion protein described above or herein. In some embodiments, the present invention provides an expression cassette comprising a polynucleotide sequence encoding the peptide or its fusion protein operably linked to a promoter. In some embodiments, the present invention provides a vector comprising such an expression cassette. In some embodiments, the present invention provides a host cell comprising such a nucleic acid, a polynucleotide coding sequence, an expression cassette, or a vector described above and herein.

In a third aspect, the present invention provides a composition, which comprises an active ingredient of the peptide described above or herein, its fusion protein, or in its conjugated form described above or herein; the nucleic acid, the expression cassette, the vector, or the host cell described above or herein, plus one or more pharmaceutically acceptable excipient. In some embodiments, the composition may optionally further include a second active ingredient, such as therapeutic agent with anti-cancer activity or anti-inflammatory activity. In some embodiments, the composition consists of or consists essentially of an active ingredient of the peptide described above or herein, its fusion protein, or in its conjugated form described above or herein; the nucleic acid, the expression cassette, the vector, or the host cell described above or herein, plus one or more pharmaceutically acceptable excipients.

In a fourth aspect, a method is provided for suppressing inflammation or for suppressing cancer cell proliferation and/or metastatic potential. The method includes the step of administering to a subject in need thereof an effective amount of the composition described above or herein. In some embodiments, the composition is administered systemically (e.g., by injection or oral ingestion) or locally (e.g., by topical application or by suppository). In some embodiments, the composition is administered to the subject by intravenous, subcutaneous, intraperitoneal, intraosseous, intramuscular, or intratumoral injection. In some embodiments, the composition is administered orally or nasally or topically. In some embodiments, the subject receiving the composition is suffering from or at risk of developing a condition involving inflammation, such as sepsis. In some embodiments, the subject receiving the composition is suffering from or at risk of developing a condition involving inappropriate cellular proliferation, such as cancer. In some embodiments, one or more signs, symptoms, and/or sequelae associated with the condition to be treated (e.g., sepsis) are mitigated in the subject.

In the fifth aspect, the present invention provides a method for identifying an inhibitor of the specific binding between MD2 and integrin αvβ3 The method includes these steps: (1) contacting integrin αvβ3 and a polypeptide comprising the amino acid sequence of SEQ ID NO:1, in the presence of a test compound, under conditions permissible for MD2-integrin αvβ3 binding; and (2) detecting the level of polypeptide-integrin αvβ3 binding, wherein a decrease in the level of binding when compared with the level of binding in the absence of the test compound indicates the test compound as an inhibitor of MD2-integrin αvβ3 binding. Conversely, if an increase in the level of binding is detected when compared with the level of binding in the absence of the test compound identifies the test compound as an enhancer of MD2-integrin αvβ3 binding. In some embodiments, the polypeptide used in the method consists of the amino acid sequence of SEQ ID NO:1. In some embodiments, the polypeptide further comprises at least one, possibly more heterologous amino acid sequence (e.g., GST or a string of 6-10 His (SEQ ID NO: 3)). In some embodiments, the integrin αvβ3 is expressed on a cell surface. In some embodiments, either one of the integrin αvβ3 and the polypeptide is immobilized on a solid substrate.

In a sixth aspect, the present invention provides a kit for inhibiting inflammation or for suppressing cancer cell proliferation. The kit includes a first container containing the composition of this invention as described above or herein and a second container containing a second therapeutic agent (e.g., another anti-inflammatory therapeutic agent or another anti-cancer therapeutic agent). Optionally, the kit further includes user instruction material providing description of dosing arrangements and its intended use.

DEFINITIONS

Figure 1:
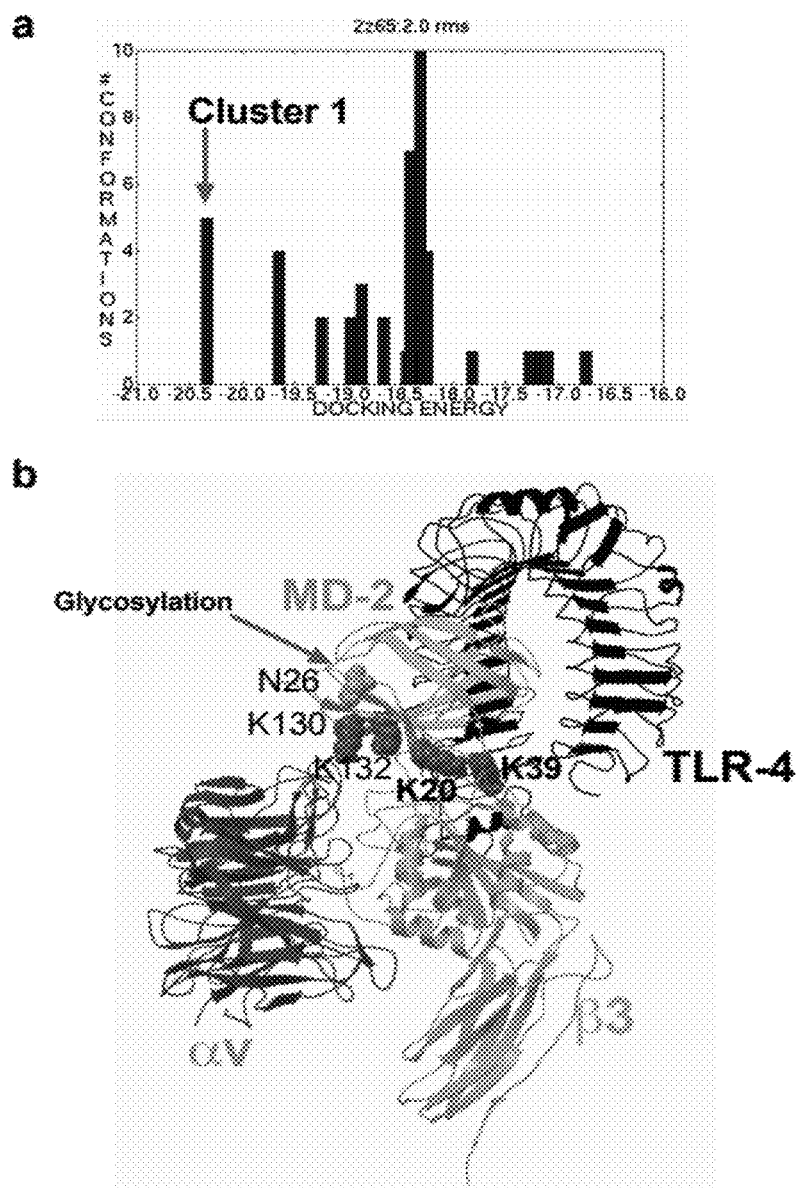
FIG. 1A model of the αvβ3-MD2-TLR4 complex. Docking simulation of the interaction between MD2 and αvβ3 using Autodock3 was performed. a. Clustering analysis of docking poses. Fifty docking poses were clustered. Cluster 1 (docking energy, −20.3 kcal/mol) was further analyzed. b. Docking model. The TLR4-MD2 complex (3fxi.pdb, black) was superposed to the integrin-MD2 (magenta) complex. The model predicts that integrin αvβ3 and TLR4 simultaneously bind to MD2 without steric hindrance. Four Lys residues at positions 20, 39, 130, 132 were selected for mutagenesis (FIG. 2). Asn26 and Asn114 are glycosylation sites. The model predicts that glycosylation does not block integrin access.
Figure 2:
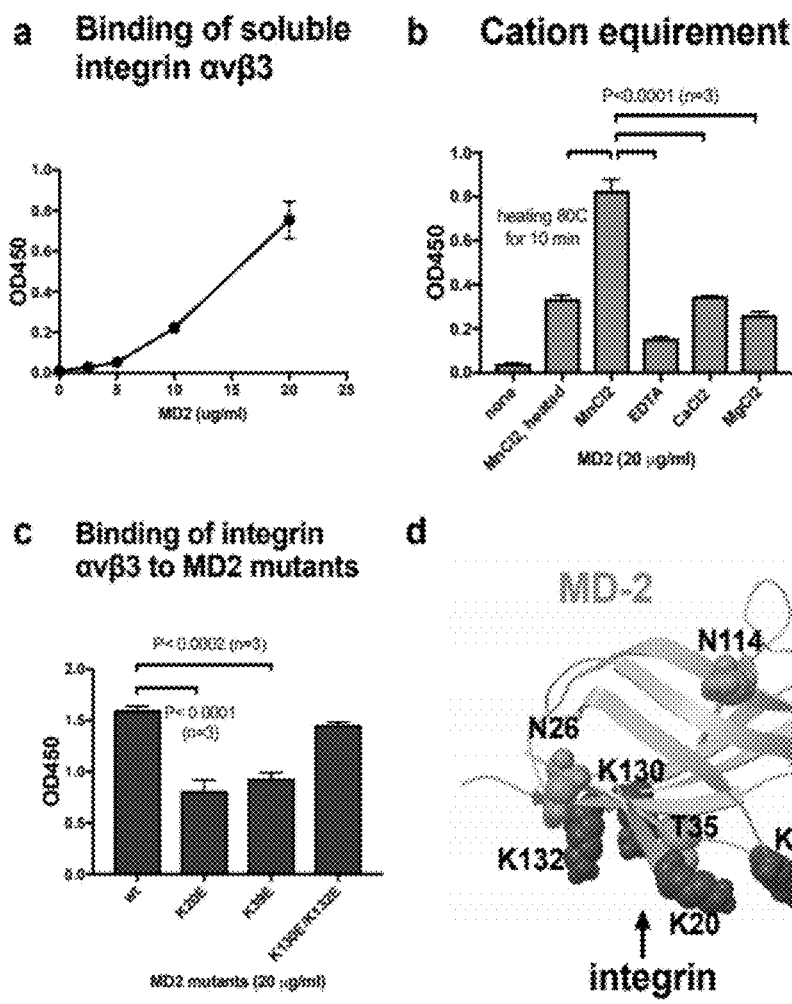
FIG. 2 Binding of MD2 to integrin αvβ3. a. Binding of soluble integrin αvβ3 to recombinant MD2 protein in ELISA-type binding assay. Wells of 96-well microtiter plate were coated with WT MD2 protein and remaining protein-binding sites were blocked with BSA. Soluble αvβ3 was added (5 μg/ml) in Tyrode-HEPES buffer with 1 mM $MnCl_2$ (to activate integrins) and incubated for 1 h at room temperature. After rinsing the wells with the buffer, bound αvβ3 was determined using HRP (horse radish peroxidase)-conjugated anti-His tag antibodies. The data indicate that αvβ3 binds to MD2 in a dose-dependent manner. b. Binding of soluble integrin αvβ3 to MD2 protein requires cations ($Mn^{2+}$>>$Mg^{2+}$ or $Ca^{2+}$) and inhibited by heat treatment (80° C. 10 min). Cations and EDTA are at 1 mM. The data indicate that αvβ3 binding to MD2 required integrin activation by $Mn^{2+}$ and proper folding, as in the case of other typical integrin ligands. c. Binding of soluble integrin αvβ3 to MD2 mutants in ELISA-type binding assay. The binding assay was performed as described in FIG. 1. The data indicate that K20E and K39E are defective in integrin binding but K130E-K132E was not, revealing that Lys20 and Lys39 are critical for integrin binding (consistent with the docking mode, FIG. 1). d. Positions of amino acid residues in MD2. K20 and K39 are critical for integrin binding. The T35A mutation that suppresses LPS signaling (Hamann et al. 2004) is in the integrin binding interface. Glycosylation (at N26 and N114) is unlikely to block integrin binding.

The terms "a," "an," and "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" as used herein shall generally mean an acceptable degree of error for the quantity measured given the nature or precision of the measurements. Typical, exemplary degrees of error are within 20 percent (%), preferably within 10%, and more preferably within 5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

The term "MD2" refers to Myeloid Differentiation factor 2 (MD2), a secretory protein also known as Lymphocyte antigen 96 (LY96). The MD2 protein appears to associate with toll-like receptor 4 (TLR4) on the cell surface and confers responsiveness to lipopolysaccharide (LPS), thus providing a link between the receptor and LPS signaling. The primary interaction between TLR4 and MD2 is formed before binding LPS. An exemplary human wild-type MD2 protein amino acid sequence is provided herein as SEQ ID NO:1. An "MD2 polynucleotide" refers to a nucleic acid sequence from the gene encoding the MD2 protein, and may include both the coding and non-coding regions. "MD2 cDNA," "MD2 mRNA," "MD2 coding sequence," and their variations refer to a nucleic acid sequence that encodes an MD2 polypeptide.

The terms "MD2 dominant negative polypeptide," "MD2 dominant negative mutant," "MD2 dominant negative mutant polypeptide," and "MD2 mutant polypeptide" refer to an MD2 antagonist compound in the form of a mutated MD2 polypeptide, or a fragment thereof, which suppresses MD2/integrin-induced MD2 cellular signaling by way of its interaction with integrins (such as integrin αvβ3) in a manner that imposes an inhibitory or disruptive effect on the specific binding among wild-type MD2 and integrins, thus inhibiting downstream events normally triggered by MD2-integrin interaction and subsequent signaling, for example, MD2-mediated inflammatory response. In an exemplary MD2 dominant negative mutant, one or more amino acid residues predicted to interact with integrin, e.g., K20 and K39 residues, are mutated, either by deletion or by substitution with a different amino acid (e.g., the K20E, K20E/K39E, and K39E mutations), resulting in the mutant having decreased or even abolished capability to bind integrin such as αvβ3. Typically, the MD2 dominant negative mutants of this invention does not include an A substitution at either or both of these residues. These MD2 dominant negative mutants can be identified based on their deficiency compared to the wild-type MD2 in decreased integrin binding, as well as in signaling functions (failure to activate inflammatory response, for example) in test cells (e.g., changes in wild-type MD2-induced NF-kB activation will be measured in HEK293 cells). In some embodiments, binding affinity for an integrin (e.g., αvβ3) and/or signaling function is decreased by at least about 10%, 20%, 30%, 40%, 50%, 60%, 70%, 80%, or 90% as compared to the wild-type MD2.

An MD2 dominant negative mutant may be initially generated based on a wild-type MD2 amino acid sequence (e.g., SEQ ID NO:1) with certain amino acid residue(s) (e.g., K20 and/or K39) mutated. In some embodiments, the MD2 dominant negative mutant comprises an amino acid sequence having at least about 80% (e.g., at least about 80%, 81%, 82%, 83%, 84%, 85%, 86%, 87%, 88%, 89%, 90%, 91%, 92%, 93%, 94%, 95%, 96%, 97%, 98%, or 99%) identity to SEQ ID NO:1 in which at least one, maybe two, of K20 and K39 are mutated. In some instances, the positions K20 and/or K39 are not used in calculating the percent identity. In some embodiments, the MD2 dominant negative mutant polypeptide comprises the amino acid sequence set forth in SEQ ID NO:1 in which at least one, maybe two, of K20 and K39 are mutated. In some embodiments, the MD2 dominant negative mutant polypeptide consists of the amino acid sequence set forth in SEQ ID NO:1 in which at least one maybe two of K20 and K39 are mutated. In some embodiments, K20 is mutated, for example, by an E but not an A. In some embodiments, K39 is mutated, for example, by an E but not an A. In some embodiments, both K20 and K39 are mutated, for example, both by an E but not an A.

Furthermore, the MD2 dominant negative mutant polypeptide may further include one or more heterologous amino acid sequences (derived from a source other than the MD2 protein) at its N-terminus and/or C-terminus. For example, an MD2 dominant negative mutant may optionally include one or more additional heterologous amino acid sequence(s) of 1, 2, 3, 4, 5, 6, 7, 8, 9, 10, 11, 12, 13, 14, 15, 16, 17, 18, 19, 20, 25, 30, 35, 40, 45, or up to 50 amino acids at the C- and/or N-terminus of the MD2-derived sequence. In some embodiments, the one or more heterologous amino acid(s) comprise a cysteine residue that is located at the N- and/or C-terminal end and may be used, for example, to attach PEG group(s). Such heterologous peptide sequences can be of a varying nature, for example, any one of the "tags" known and used in the field of recombinant proteins: a peptide tag such as an AviTag, a peptide allowing biotinylation by the enzyme BirA and so the protein can be isolated by streptavidin, a Calmodulin-tag, a peptide bound by the protein calmodulin, a polyglutamate tag, a peptide binding efficiently to anion-exchange resin such as Mono-Q, an E-tag, a peptide recognized by an antibody, a FLAG-tag, a peptide recognized by an antibody, an HA-tag, a peptide recognized by an antibody, a His-tag, 5-10 histidines bound by a nickel or cobalt chelate, a Myc-tag, a short peptide recognized by an antibody, an S-tag, an SBP-tag, a peptide that specifically binds to streptavidin, a Softag 1 for mammalian expression, a Softag 3 for prokaryotic expression, a Strep-tag, a peptide that binds to streptavidin or the modified streptavidin called streptactin (Strep-tag II), a TC tag, a tetracysteine tag that is recognized by FlAsH and ReAsH biarsenical compounds, a V5 tag, a peptide recognized by an antibody, a VSV-tag, a peptide recognized by an antibody, an Xpress tag; or a covalent peptide tags such as an Isopeptag, a peptide that binds covalently to pilin-C protein, a SpyTag, a peptide that binds covalently to SpyCatcher protein; or a protein tag such as a BCCP tag (Biotin Carboxyl Carrier Protein), a protein domain biotinylated by BirA enabling recognition by streptavidin, a Glutathione-S-transferase (GST) tag, a protein that binds to immobilized glutathione, a Green fluorescent protein (GFP) tag, a protein that is spontaneously fluorescent and can be bound by nanobodies, a Maltose binding protein (MBP) tag, a protein that binds to amylose agarose, a Nus-tag, a Thioredoxin-tag, an Fc-tag (derived from immunoglobulin Fc domain, allowing dimerization and solubilization), a tag that can be used for purification on Protein-A Sepharose; as well as other types of tags such as the Ty tag. Furthermore, the MD2 dominant negative mutants may also include one or more D-amino acids or include chemical modifications such as PEGylation, myristoylation, glycosylation, crosslinking, and the like.

In some embodiments, the MD2 dominant negative mutant polypeptide is present as part of a fusion protein, e.g., a fusion protein comprising an MD2 dominant negative mutant polypeptide described herein and an Fc polypeptide. As used herein, the term "Fc polypeptide" refers to the C-terminal region of an immunoglobulin heavy chain polypeptide. An Fc polypeptide typically contains constant region sequences (e.g., the CH2 domain and/or the CH3 domain) and may also contain the hinge region (or a portion thereof). An Fc polypeptide typically does not contain a variable region. In some embodiments, the Fc polypeptide is an IgG1, IgG2, IgG3, or IgG4 Fc polypeptide.

Furthermore, the fusion protein may be labeled, e.g., with a radionuclide. The term "radionuclide" is intended to include any nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance. Examples of radionuclides suitable for use in the present invention include, but are not limited to, fluorine 18 ($^{18}F$), phosphorus 32 ($^{32}P$), scandium 47 ($^{47}Sc$), cobalt 55 ($^{55}Co$), copper 60 ($^{60}Cu$), copper 61 ($^{61}Cu$), copper 62 ($^{62}Cu$), copper 64 ($^{64}Cu$), gallium 66 ($^{66}Ga$), copper 67 ($^{67}Cu$), gallium 67 ($^{67}Ga$), gallium 68 ($^{68}Ga$), rubidium 82 ($^{82}Rb$), yttrium 86 ($^{86}Y$), yttrium 87 ($^{87}Y$), strontium 89 ($^{89}Sr$), yttrium 90 ($^{90}Y$), rhodium 105 ($^{105}Rh$) silver 111 ($^{111}Ag$), indium 111 ($^{111}In$) iodine 124 ($^{124}I$), iodine 125 ($^{125}I$), iodine 131 ($^{131}I$), tin 117m ($^{117m}Sn$), technetium 99m ($^{99m}Tc$), promethium 149 ($^{149}Pm$), samarium 153 ($^{153}Sm$), holmium 166 ($^{166}Ho$) lutetium 177 ($^{177}Lu$), rhenium 186 ($^{186}Re$), rhenium 188 ($^{188}Re$), thallium 201($^{201}Tl$), astatine 211 ($^{211}At$) and bismuth 212 ($^{212}Bi$). As used herein, the "m" in $^{117m}Sn$ and $^{99m}Tc$ stands for the meta state. Additionally, naturally-occurring radioactive elements such as uranium, radium, and thorium, which typically represent mixtures of radioisotopes, are suitable examples of radionuclides. $^{67}Cu$, $^{131}I$, $^{177}Lu$, and $^{186}Re$ are beta- and gamma-emitting radionuclides. $^{212}Bi$ is an alpha- and beta-emitting radionuclide. $^{211}At$ is an alpha-emitting radionuclide. $^{32}P$, $^{47}Sc$, $^{89}Sr$, $^{90}Y$, $^{105}Rh$, $^{111}Ag$, $^{117m}Sn$, $^{149}Pm$, $^{153}Sm$, $^{166}Ho$, and $^{188}Re$ are examples of beta-emitting radionuclides. $^{67}Ga$ $^{111}In$, $^{99m}Tc$, and $^{201}$Tl are examples of gamma-emitting radionuclides. $^{55}$Co, $^{60}$Cu, $^{61}$Cu, $^{62}$Cu, $^{66}$Ga, $^{68}$Ga, $^{82}$Rb, and $^{86}$Y are examples of positron-emitting radionuclides. $^{64}$Cu is a beta- and positron-emitting radionuclide.

In some embodiments, a modification such as PEGylation or myristoylation, or fusion to an Fc polypeptide, increases the half-life (e.g., in the body of a subject such as a mammal) of the polypeptide, as compared to a corresponding MD2 dominant negative mutant polypeptide that does not have the modification of that is not fused to the Fc polypeptide. Increased half-life can be due to, for example, increased stability (i.e., the polypeptide is more resistant to degradation and/or metabolism) and/or decreased clearance (e.g., renal clearance). In some embodiments, half-life of the modified (e.g., PEGylated and/or myristoylated) polypeptide is increased by at least about 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 15-fold, 20-fold, 25-fold, 30-fold, 35-fold, 40-fold, 45-fold, 50-fold, 60-fold, 70-fold, 80-fold, 90-fold, 100-fold, or more.

The term "inhibiting" or "inhibition," as used herein, refers to any detectable negative effect on a target biological process, such as the binding between MD2 and integrin αvβ3, or on its downstream processes including NF-kB activation, as well as inflammatory response including sepsis or cellular proliferation. Typically, an inhibition is reflected in a decrease of at least 10%, 20%, 30%, 40%, 50%, 60%, 70%, 80% or higher in MD2-integrin binding, or any one of the downstream parameters mentioned above, when compared to a control.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, whereas non-naturally occurring amino acids include D-amino acids and those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a mutant MD2 amino acid sequence has at least 80% identity, preferably 85%, 90%, 91%, 92%, 93, 94%, 95%, 96%, 97%, 98%, 99%, or 100% identity, to a reference sequence, e.g., a wild-type MD2 protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990)*J Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

The term "inflammation" refers to an organism's (e.g., a mammal's) immune response to irritation, toxic substances, pathogens, or other stimuli. The response can involve innate immune components and/or adaptive immunity. Inflammation is generally characterized as either chronic or acute. Acute inflammation can be characterized by, as non-limiting examples, redness, pain, heat, swelling, and/or loss of function due to infiltration of plasma proteins and leukocytes to the affected area. Chronic inflammation can be characterized by, as non-limiting examples, persistent inflammation, tissue destruction, and/or attempts at repair. Monocytes, macrophages, plasma B cells, and other lymphocytes are commonly recruited to the affected area, and angiogenesis and fibrosis can occur, in some instances leading to scar tissue.

The term "inflammatory condition" or "inflammatory disorder" refers to a condition or disorder that is characterized or exacerbated by an inflammatory response, as described above. A list of exemplary inflammatory conditions includes: systemic lupus erythematosus (SLE), diabetes, chronic renal disease, asthma, autoimmune disease, chronic inflammation, chronic prostatitis, glomerulonephritis, hypersensitivities and allergies, skin disorders such as eczema, inflammatory bowel disease, pelvic inflammatory disease, reperfusion injury, rheumatoid arthritis, transplant rejection, and vasculitis.

The term "sepsis" refers to a serious, potentially life-threatening, condition that is caused by an extreme response to an infection. In some instances, sepsis may lead to extravasation, shock (e.g., hypovolemic and/or distributive shock), respiratory failure, tachypnea, bradypnea, abnormal blood clotting, or death. Signs and symptoms associated with sepsis include, but are not limited to, altered mental status, respiratory distress, hypoxia, cyanosis, hypotension, cardiac arrhythmia (e.g., tachycardia, bradycardia), acidosis (e.g., metabolic, respiratory), fever, and rash.

The term "cancer" refers to any of various malignant neoplasms characterized by the proliferation of anaplastic cells that tend to invade surrounding tissue and metastasize to new body sites. Non-limiting examples of different types of cancer suitable for treatment using the compositions and methods of the present invention include colorectal cancer, colon cancer, anal cancer, liver cancer, ovarian cancer, breast cancer, lung cancer, bladder cancer, thyroid cancer, pleural cancer, pancreatic cancer, cervical cancer, prostate cancer, testicular cancer, bile duct cancer, gastrointestinal carcinoid tumors, esophageal cancer, gall bladder cancer, rectal cancer, appendix cancer, small intestine cancer, stomach (gastric) cancer, renal cancer (e.g., renal cell carcinoma), cancer of the central nervous system, skin cancer, oral squamous cell carcinoma, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma.

The term "heterologous," as used in the context of describing the relative location or position of two elements, such as two polynucleotide sequences (e.g., a promoter and a polypeptide-encoding sequence) or polypeptide sequences (e.g., a first amino acid sequence (such as one set forth in SEQ ID NO:1 with a mutation or mutations) and a second peptide sequence serving as a fusion partner with the first amino acid sequence), means that the two elements are not naturally found in the same relative location or position. Thus, a "heterologous promoter" of a gene refers to a promoter that is not naturally operably linked to that gene. Similarly, a "heterologous polypeptide/amino acid sequence" or "heterologous polynucleotide" to an MD2 amino acid sequence or its encoding sequence is one derived from a non-MD2 origin.

A composition "consisting essentially of an MD2 dominant negative mutant" is one that includes an MD2 mutant that inhibits specific binding between wild-type MD2 and integrin (such as integrin αvβ3) but no other compounds that contribute significantly to the inhibition of such binding. Such compounds may include inactive excipients, e.g., for formulation or stability of a pharmaceutical composition, or active ingredients that do not significantly contribute to the inhibition of MD2-integrin binding. Exemplary compositions consisting essentially of an MD2 dominant negative mutant include therapeutics, medicaments, and pharmaceutical compositions.

The term "subject" or "subject in need of treatment" refers to an individual who seeks medical attention due to risk of, or actual sufferance from, a condition involving undesirable inflammation (e.g., sepsis) or a condition involving unregulated cell proliferation (e.g., cancer). The term subject can include both animals, especially mammals, and humans. Subjects or individuals in need of treatment include those that demonstrate symptoms of an inflammatory disorder or cancer or those are at risk of later developing the disease or disorder and/or its symptoms.

DETAILED DESCRIPTION OF THE INVENTION

I. Introduction

Efforts have been made to develop dominant-negative MD2 mutants using a strategy that was successfully used to develop mutants of other proteins that normally participate in an integrin-containing signaling complex. The mutants have diminished ability to bind integrin while retaining the ability to bind other members of the signaling complex and therefore act as dominant-negative mutants to the wild-type protein in suppressing signaling mediated by the wild-type protein and integrin. The potential of such dominant-negative mutants as therapeutic agents against the downstream events of cellular signaling mediated by the wild-type protein, such as inflammation, is explored.

II. Production of Mutant MD2 Polypeptides

A. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of an MD2 gene, a polynucleotide encoding a polypeptide having the amino acid sequence SEQ ID NO:1, and synthetic oligonucleotides can be verified after cloning or subcloning using, e.g., the chain termination method for sequencing double-stranded templates of Wallace et al., *Gene* 16: 21-26 (1981).

B. Coding Sequence for an MD2 Mutant Polypeptide

Polynucleotide sequences encoding a wild-type MD2 protein, especially a wild-type human MD2 protein, have been determined and may be obtained from a commercial supplier. For example, the GenBank Accession Nos. for human MD2 mRNA and protein sequences are AB446498 and Q9Y6Y9, respectively.

The rapid progress in the studies of human genome has made possible a cloning approach where a human DNA sequence database can be searched for any gene segment that has a certain percentage of sequence homology to a known nucleotide sequence, such as one encoding a previously identified human MD2 protein. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a human MD2 protein can be isolated from a human cDNA or genomic DNA library using standard cloning techniques such as polymerase chain reaction (PCR), where homology-based primers can often be derived from a known nucleic acid sequence encoding an MD2. Most commonly used techniques for this purpose are described in standard texts, e.g., Sambrook and Russell, supra.

cDNA libraries suitable for obtaining a coding sequence for a human MD2 may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene*, 25: 263-269 (1983); Ausubel et al., supra). Upon obtaining an amplified segment of nucleotide sequence by PCR, the segment can be further used as a probe to isolate the full length polynucleotide sequence encoding the MD2 from the cDNA library. A general description of appropriate procedures can be found in Sambrook and Russell, supra.

A similar procedure can be followed to obtain a full-length sequence encoding a human MD2 from a human genomic library. Human genomic libraries are commercially available or can be constructed according to various art-recognized methods. In general, to construct a genomic library, the DNA is first extracted from a tissue where an MD2 is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science*, 196: 180-182 (1977). Colony hybridization is carried out as described by Grunstein et al., *Proc. Natl. Acad. Sci. USA*, 72: 3961-3965 (1975).

Based on sequence homology, degenerate oligonucleotides can be designed as primer sets and PCR can be performed under suitable conditions (see, e.g., White et al., *PCR Protocols: Current Methods and Applications*, 1993; Griffin and Griffin, *PCR Technology*, CRC Press Inc. 1994) to amplify a segment of nucleotide sequence from a cDNA or genomic library. Using the amplified segment as a probe, the full-length nucleic acid encoding an MD2 is obtained.

Upon acquiring a nucleic acid sequence encoding an MD2 protein, the coding sequence can be further modified by a number of well-known techniques such as restriction endonuclease digestion, PCR, and PCR-related methods to generate coding sequences for MD2 mutants (especially the dominant-negative type). The polynucleotide sequence encoding a desired MD2 mutant polypeptide can then be subcloned into a vector, for instance, an expression vector, so that a recombinant polypeptide can be produced from the resulting construct. Further modifications to the coding sequence, e.g., nucleotide substitutions, may be subsequently made to alter the characteristics of the polypeptide.

A variety of mutation-generating protocols are established and described in the art, and can be readily used to modify a polynucleotide sequence encoding an MD2-related polypeptide. See, e.g., Zhang et al., *Proc. Natl. Acad. Sci. USA*, 94: 4504-4509 (1997); and Stemmer, *Nature*, 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortie, *Science*, 229: 1193-1201 (1985)), mutagenesis using uracil-containing templates (Kunkel, *Proc. Natl. Acad. Sci. USA*, 82: 488-492 (1985)), oligonucleotide-directed mutagenesis (Zoller and Smith, *Nucl. Acids Res.*, 10: 6487-6500 (1982)), phosphorothioate-modified DNA mutagenesis (Taylor et al., *Nucl. Acids Res.*, 13: 8749-8764 and 8765-8787 (1985)), and mutagenesis using gapped duplex DNA (Kramer et al., *Nucl. Acids Res.*, 12: 9441-9456 (1984)).

Other possible methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond. A*, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

C. Modification of Nucleic Acids for Preferred Codon Usage in a Host Organism The polynucleotide sequence encoding an MD2 mutant polypeptide can be further altered to coincide with the preferred codon usage of a particular host. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of the MD2 mutant polypeptides.

D. Chemical Synthesis of MD2 Mutant Polypeptides

The amino acid sequence of human MD2 protein is provided. An MD2 mutant polypeptide comprising one or more point mutants in the wild-type MD2 amino acid sequence thus can also be chemically synthesized using conventional peptide synthesis or other protocols well known in the art.

Polypeptides may be synthesized by solid-phase peptide synthesis methods using procedures similar to those described by Merrifield et al., *J. Am. Chem. Soc.*, 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., *Solid Phase Peptide Synthesis: A Practical Approach*, IRL Press (1989), and Bodanszky, *Peptide Chemistry, A Practical Textbook*, 2nd Ed., Springer-Verlag (1993)).

III. Expression and Purification of MD2 Mutant Polypeptides

Following verification of the coding sequence, an MD2 mutant polypeptide of the present invention can be produced using routine techniques in the field of recombinant genetics, relying on the polynucleotide sequences encoding the polypeptide disclosed herein.

A. Expression Systems

To obtain high level expression of a nucleic acid encoding an MD2 mutant polypeptide of the present invention, one typically subclones a polynucleotide encoding the polypeptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the polypeptide are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the MD2 mutant polypeptide in host cells. A typical expression cassette thus contains a promoter operably linked to the nucleic acid sequence encoding the MD2 mutant polypeptide and signals required for efficient polyadenylation of the transcript, ribosome binding sites, and translation termination. The nucleic acid sequence encoding the MD2 mutant polypeptide is typically linked to a cleavable signal peptide sequence to promote secretion of the polypeptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/$A^+$, pMT010/$A^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the MD2 mutant polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., an MD2 mutant polypeptide of the present invention) is desired, the expression vector further comprises a sequence encoding a secretion signal, such as the E. coli OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

A person skilled in the art will recognize that various conservative substitutions can be made to any wild-type MD2 polypeptide, to produce an MD2 mutant polypeptide that, while still retaining the ability to bind LPS or TLR4, does not trigger MD2-integrin downstream signaling. Moreover, modifications of a polynucleotide coding sequence may also be made to accommodate preferred codon usage in a particular expression host without altering the resulting amino acid sequence.

B. Transfection Methods

Standard transfection methods are used to produce bacterial, mammalian, yeast, insect, or plant cell lines that express large quantities of an MD2 mutant polypeptide, which are then purified using standard techniques (see, e.g., Colley et al., *J. Biol. Chem.* 264: 17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the MD2 mutant polypeptide.

C. Purification of Recombinantly Produced MD2 Mutant Polypeptides

Once the expression of a recombinant MD2 mutant polypeptide in transfected host cells is confirmed, e.g., via an immunoassay such as Western blotting assay, the host cells are then cultured in an appropriate scale for the purpose of purifying the recombinant polypeptide.

1. Purification of Recombinantly Produced Polypeptides from Bacteria

When the MD2 mutant polypeptides of the present invention are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, NY). Alternatively, the cells can be sonicated on ice. Additional methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., an MD2 mutant polypeptide, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide of the present invention, e.g., an MD2 mutant polypeptide, is expressed in host cells in a soluble form, its purification can follow the standard protein purification procedure described below. This standard purification procedure is also suitable for purifying MD2 mutant polypeptides obtained from chemical synthesis.

i. Solubility Fractionation

Often as an initial step, and if the protein mixture is complex, an initial salt fractionation can separate many of the unwanted host cell proteins (or proteins derived from the cell culture media) from the recombinant protein of interest, e.g., an MD2 mutant polypeptide of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., an MD2 mutant polypeptide. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

iii. Column Chromatography

The proteins of interest (such as an MD2 mutant polypeptide of the present invention) can also be separated from other proteins on the basis of their size, net surface charge, hydrophobicity, or affinity for ligands. In addition, antibodies raised against a segment of MD2 (e.g., a segment outside of the integrin-binding domain) can be conjugated to column matrices and the MD2 mutant polypeptide immunopurified. All of these methods are well-known in the art.

It will be apparent to one of skill that chromatographic techniques can be performed at any scale and using equipment from many different manufacturers (e.g., Pharmacia Biotech).

IV. Identification of Inhibitors for MD2-Integrin Binding

A. MD2-Integrin Binding Assays

An in vitro assay can be used to detect MD2-integrin binding and to identify compounds that are capable of inhibiting MD2-integrin binding. In general, such an assay can be performed in the presence of an MD2, such as human MD2, and an integrin, such as $\alpha v \beta 3$ that are known to bind each other, under conditions permitting such binding. For convenience, one of the binding partners may be immobilized onto a solid support and/or labeled with a detectable moiety. A third molecule, such as an antibody (which may include a detectable label) to one of the binding partners, can also be used to facilitate detection.

In some cases, the binding assays can be performed in a cell-free environment; whereas in other cases, the binding assays can be performed on cell surface, frequently using cells recombinantly or endogenously expressing an appropriate integrin molecule. More details and some examples of such binding assays can be found in the Examples section of this application.

To screen for compounds capable of inhibiting MD2-integrin binding, the above-described assays are performed both in the presence and absence of a test compound, the level of MD2-integrin binding is then compared. If MD2-integrin binding is suppressed at the presence of the test compound at a level of at least 10%, more preferably at least 20%, 30%, 40%, or 50%, or even higher, the test compound is then deemed an inhibitor of MD2-integrin binding and may be subject to further testing to confirm its ability to inhibit MD2 signaling.

The binding assay is also useful for determining whether or not a polypeptide derived from a wild-type MD2 protein can effectively and specifically bind integrin. For instance, a polypeptide comprising the amino acid sequence of an MD2 protein with one or more point mutations (e.g., at residue 20 or 39) may be recombinantly expressed, purified, and placed in a binding assay with integrin $\alpha v \beta 3$, substituting a full length wild type MD2 protein, which is used in a control assay to provide a comparison basis. If deemed to have sufficient integrin-binding ability, a polypeptide comprising an MD2-integrin binding sequence can then be used, in place of a wild-type full length MD2 protein, in a binding assay for identifying inhibitors of MD2-integrin binding. Conversely, an MD2 mutant that has lost or greatly diminished its integrin-binding capability may be further tested for its dominant negative features. Similarly, a polypeptide comprising a core sequence with a high level of homology (e.g., 90%, 95%, 97%, 98%, 99% or higher) to the sequence of a wild-type MD2 protein can be tested and, if appropriate, can be used, in place of a wild-type full length MD2 protein, in a binding assay for identifying inhibitors of MD2-integrin binding. Such a variant of MD2 protein may also be tested for its potential dominant negative features and utilities.

Inhibitors of MD2-integrin binding can have diverse chemical and structural features. For instance, an inhibitor can be a non-functional MD2 mutant that retaining integrin-binding ability, an antibody to either MD2 or integrin that interferes with MD2-integrin binding, or any small molecule or macromolecule that simply hinders the interaction between MD2 and integrin. Essentially any chemical compound can be tested as a potential inhibitor of MD2-integrin binding. Most preferred are generally compounds that can be dissolved in aqueous or organic (especially DMSO-based) solutions. Inhibitors can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science,* 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514).

B. MD2 Signaling Assays

The inhibitors of MD2-integrin binding are useful for their ability to inhibit MD2 signaling, especially as anti-inflammation or anti-cancer therapeutics. Assays for confirming such inhibitory effect of an inhibitor can be performed in vitro or in vivo. An in vitro assay typically involves exposure of cultured cells to an inhibitor and monitoring of subsequent biological and biochemical changes in the cells. For example, following exposure to 0.1-20 μg/ml an inhibitor for 0.5-48 hours, suitable cells (such as those expressing integrin αvβ3) are examined for their proliferation/survival status using methods such as direct cell number counting, BrdU or $H^3$-thymidine incorporation, tetrazolium salt 3,[4,5-dimethylthiazol-2-yl]-2,5-diphenyltetrazolium bromide (MTT) cell proliferation assay, 3-(4,5-dimethylthiazol-2-yl)-5-(3-carboxymethoxyphenyl)-2-(4-sulfophenyl)-2H-tetrazolium (MTS) cell proliferation assay, chicken embryo allantoic membrane (CAM) assay, TUNNEL assay, annexin V binding assay, etc. Further downstream changes due to MD2 signaling, e.g., changes in NF-kB activation induced by wild-type MD2, can also be monitored to provide an indication of suppressed MD2 signaling. In addition, tumorigenicity of cancer cells is useful parameters for monitoring and can be tested by methods such as colony formation assays or soft agar assays. Detailed description of some exemplary assays can be found in the Examples section of this disclosure. An inhibitory effect is detected when a decrease in MD2 signaling, as indicated by any one aforementioned parameter, of at least 10%, 20%, 30%, 40%, 50%, 60%, 70%, 80%, 90% or more is observed.

The effects of an MD2-integrin binding inhibitor of the present invention can also be demonstrated in in vivo assays. For example, an inhibitor of MD2-integrin can be injected into animals that have a compromised immune system (e.g., nude mice, SCID mice, or NOD/SCID mice) and therefore permit xenograft tumors. Injection methods can be intravenous, intraperitoneal, or intratumoral in nature. Tumor development is subsequently monitored by various means, such as measuring tumor volume and scoring secondary lesions due to metastases, in comparison with a control group of animals with similar tumors but not given the inhibitors. Similarly, in vivo assays can be performed in an inflammation animal model to test and verify the capability of an MD2 mutant in inhibiting inflammatory response induced by MD2-integrin signaling. An inhibitory effect is detected when a negative effect on tumor growth or metastasis is established in the test group. Preferably, the negative effect is at least a 10% decrease; more preferably, the decrease is at least 20%, 30%, 40%, 50%, 60%, 70%, 80%, or 90%.

V. Pharmaceutical Compositions and Administration

The present invention also provides pharmaceutical compositions or physiological compositions comprising an effective amount of a compound that inhibits MD2-integrin binding, such as a dominant negative MD2 mutant K20E, K39E, or K20E/K39E, or its encoding nucleic acid, inhibiting MD2 signaling in both prophylactic and therapeutic applications. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, PA, 17th ed. (1985). For a brief review of methods for drug delivery, see, Langer, *Science* 249: 1527-1533 (1990).

The pharmaceutical compositions of the present invention can be administered by various routes, e.g., oral, nasal, subcutaneous, transdermal, intramuscular, intravenous, or intraperitoneal. The preferred routes of administering the pharmaceutical compositions are local delivery to an organ or tissue suffering from a condition exacerbated by overactivation of MD2-integrin signaling (e.g., intratumor injection to a tumor) at daily doses of about 0.01-5000 mg, preferably 5-500 mg, of an MD2-integrin binding inhibitor for a 70 kg adult human per day. The appropriate dose may be administered in a single daily dose or as divided doses presented at appropriate intervals, for example as two, three, four, or more subdoses per day.

For preparing pharmaceutical compositions containing an MD2-integrin inhibitor, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an MD2 dominant negative mutant polypeptide. In tablets, the active ingredient (an inhibitor of MD2-integrin binding) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of an inhibitor of MD2-integrin binding. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of an MD2-integrin binding inhibitor with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., a dominant-negative MD2 mutant polypeptide) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., an MD2-integrin binding inhibitor) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing MD2-integrin binding inhibitors can be administered for prophylactic and/or therapeutic treatments. In therapeutic applications, compositions are administered to a patient already suffering from a condition that may be exacerbated by overactivation of MD2-integrin signaling in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of the inhibitor per day for a 70 kg patient, with dosages of from about 5 mg to about 500 mg of the inhibitor per day for a 70 kg patient being more commonly used.

In prophylactic applications, pharmaceutical compositions containing MD2-integin binding inhibitors are administered to a patient susceptible to or otherwise at risk of developing a disease or condition in which undesirable overactivation of MD2-integrin signaling is present, in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,000 mg of the inhibitor for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should provide a quantity of an MD2-integrin binding sufficient to effectively inhibit MD2 signaling in the patient, either therapeutically or prophylactically.

VI. Therapeutic Applications Using Nucleic Acids

A variety of diseases can be treated by therapeutic approaches that involve introducing a nucleic acid encoding a polypeptide inhibitor of integrin-MD2 binding into a cell such that the coding sequence is transcribed and the polypeptide inhibitor is produced in the cell. Diseases amenable to treatment by this approach include a broad spectrum of inflammatory diseases and disorders as well as cancers, the survival, growth, and metastasis of which rely on to some extent the continued signaling of MD2 or integrin family members. For discussions on the application of gene therapy towards the treatment of genetic as well as acquired diseases, see, Miller *Nature* 357:455-460 (1992); and Mulligan *Science* 260:926-932 (1993).

A. Vectors for Gene Delivery

For delivery to a cell or organism, a polynucleotide encoding a polypeptide that inhibits MD2-integrin binding (such as the dominant-negative mutant K20E, K39E, or K20E/K39E) can be incorporated into a vector. Examples of vectors used for such purposes include expression plasmids capable of directing the expression of the nucleic acids in the target cell. In other instances, the vector is a viral vector system wherein the polynucleotide is incorporated into a viral genome that is capable of transfecting the target cell. In a preferred embodiment, the polynucleotide encoding a polypeptide inhibitor can be operably linked to expression and control sequences that can direct expression of the polypeptide in the desired target host cells. Thus, one can achieve expression of the polypeptide inhibitor under appropriate conditions in the target cell.

B. Gene Delivery Systems

Viral vector systems useful in the expression of a polypeptide inhibitor of MD2-integrin binding include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the genes of interest (e.g., one encoding for a polypeptide inhibitor of the present invention) are inserted into such vectors to allow packaging of the gene construct, typically with accompanying viral DNA, followed by infection of a sensitive host cell and expression of the gene of interest.

As used herein, "gene delivery system" refers to any means for the delivery of a nucleic acid of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO/9406922), synthetic peptides mimicking influenza virus hemagglutinin (Plank et al., *J. Biol. Chem.* 269:12918-12924 (1994)), and nuclear localization signals such as SV40 T antigen (WO93/19768).

Retroviral vectors may also be useful for introducing the coding sequence of a polypeptide inhibitor of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.*, 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. 4,405,712, Gilboa *Biotechniques* 4:504-512 (1986); Mann et al., *Cell* 33:153-159 (1983); Cone and Mulligan *Proc. Natl. Acad. Sci. USA* 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, a polypeptide or polynucleotide of the invention and thus restore the cells to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA,* 81:6349-6353 (1984); Danos and Mulligan *Proceedings of the National Academy of Sciences, USA,* 85:6460-6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

C. Pharmaceutical formulations

When used for pharmaceutical purposes, the nucleic acid encoding an MD2-integrin binding inhibitor polypeptide is generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's *Pharmaceutical Sciences*, Mack Publishing Company, Philadelphia, PA, 17th ed. (1985).

D. Administration of Formulations

The formulations containing a nucleic acid encoding a polypeptide inhibitor of the binding between MD2 and integrin can be delivered to any tissue or organ using any delivery method known to the ordinarily skilled artisan. In some embodiments of the invention, the nucleic acids encoding the inhibitor polypeptides are formulated for systemic administration such as oral or nasal administration or injection, e.g., intravenous, intraperitoneal, subquetaneous, or intramuscular injection, for local delivery such as topical application, delivery by suppository, or intratumor injection.

The formulations containing the nucleic acid of the invention are typically administered to a cell. The cell can be provided as part of a tissue, such as an epithelial membrane, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, ultrasound, electroporation, or biolistics. In further embodiments, the nucleic acids are taken up directly by the tissue of interest.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci. USA* 93(6):2414-9 (1996); Koc et al., *Seminars in Oncology* 23(1):46-65 (1996); Raper et al., *Annals of Surgery* 223(2): 116-26 (1996); Dalesandro et al., *J. Thorac. Cardi. Surg.,* 11(2):416-22 (1996); and Makarov et al., *Proc. Natl. Acad. Sci. USA* 93(1):402-6 (1996).

Effective dosage of the formulations will vary depending on many different factors, including means of administration, target site, physiological state of the patient, and other medicines administered. Thus, treatment dosages will need to be titrated to optimize safety and efficacy. In determining the effective amount of the vector to be administered, the physician should evaluate the particular nucleic acid used, the disease state being diagnosed; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector. To practice the present invention, doses ranging from about 10 ng-1 g, 100 ng-100 mg, 1 μg-10 mg, or 30-300 μg DNA per patient are typical. Doses generally range between about 0.01 and about 50 mg per kilogram of body weight, preferably between about 0.1 and about 5 mg/kg of body weight or about $10^8$-$10^{10}$ or $10^{12}$ particles per injection. In general, the dose equivalent of a naked nucleic acid from a vector is from about 1 μg-100 μg for a typical 70 kg patient, and doses of vectors which include a retroviral particle are calculated to yield an equivalent amount of nucleic acid encoding a polypeptide that inhibits the binding between integrin and MD2 (e.g., human MD2).

VII. KITS

The invention also provides kits for inhibiting MD2 signaling according to the method of the present invention. The kits typically include a container that contains a pharmaceutical composition having an effective amount of an inhibitor of MD2-integrin binding (such as a dominant-negative mutant K20E, K39E, or K20E/K39E polypeptide or a polynucleotide sequence encoding the polypeptide) as well as informational material containing instructions on how to dispense the pharmaceutical composition, including description of the type of patients who may be treated (e.g., patients with an inflammatory condition, such as sepsis, or cancer with over-activated MD2-integrin signaling), the schedule (e.g., dose and frequency) and route of administration, and the like.

EXAMPLES

The following examples are provided by way of illustration only and not by way of limitation. Those of skill in the art will readily recognize a variety of non-critical parameters that could be changed or modified to yield essentially the same or similar results.

Example 1

Abstract

During sepsis, bacterial endotoxin (LPS) binds to Myeloid Differentiation factor 2 (MD2), a secretory protein also known as Lymphocyte antigen 96 (LY96), and the MD2/LPS complex binds to Toll-like receptor 4 (TLR4) on the epithelial cells and innate immune cells such as monocytes. TLR4 signaling results in activation of NF-kB and pro-inflammatory cytokine production, leading ultimately to cytokine storm and multiple organ failure. Plasma MD2 levels increase in sepsis, MD2 is thus a drug target for sepsis. Several small compounds/peptides based on the LPS-MD2-TLR4 complex and LPS analogues that block LPS binding to MD2 have been reported but they are still not available in clinic. These compounds target LPS-MD2 binding or MD2-TLR4 binding. Biologicals based on MD2 have not been studied. Previous studies showed that antagonists to integrin αvβ3 block TLR4 signaling from LPS, and that integrin αvβ3 is associated with the LPS/MD2/TLR4 complex. However, the specifics of the role of integrin αvβ3 are unclear. To identify the role of integrin αvβ3 in MD2-TLR4 signaling, docking simulation of interaction between integrin αvβ3 and MD2 was performed. The simulation shows that MD2 directly binds to integrin αvβ3 without steric hindrance between TLR4 and αvβ3 indicating that αvβ3 MD2, and TLR4 can stay together, making ternary complex. It was discovered that αvβ3 directly binds to MD2 in ELISA-type binding assays, and the integrin-binding sites in MD2 were identified by introducing point mutations in the potential integrin-binding site in MD2. The integrin-binding site in MD2 does not overlap with that of TLR4-binding site in MD2, consistent with the prediction. Such MD2 mutants show specificity and affinity comparable to that of WT MD2, and are defective in signaling functions. Such MD2 mutants can act as antagonists for LPS/TLR4 signaling in vitro and in animal models of sepsis. The immediate goal is to identify the role of integrin αvβ3 in LPS/MD2/TLR4 signaling using MD2 mutants as a tool. Second goal is to develop potential antagonists for this signaling pathways from MD2 mutants defective in integrin binding. To achieve these goals, the ability of human MD2 mutants as a dominant negative antagonist is studied in attenuating LPS/TLR4/MD2 signaling in monocytes and in HEK293 NF-kB reporter cells that express TLR4/MD2/CD14. Also, the ability of human MD2 mutants to suppress LPS/TLR4 signaling is studied in a sepsis model using humanized TLR4/MD2 transgenic mice.

SPECIFIC AIMS

During sepsis, bacterial endotoxin (LPS) binds to MD2. The MD-2/LPS complex in turn binds to TLR4 on the epithelial cells and innate immune cells such as monocytes. TLR4 signaling results in activation of NF-kB and pro-inflammatory cytokine production, leading ultimately to cytokine storm and multiple organ failure. Plasma MD2 levels increase in sepsis. MD2 is thus a drug target for sepsis. Several small compounds/peptides based on the LPS-MD2-TLR4 complex and LPS analogues that block LPS binding to MD2 have been reported but they are still not available in clinic. These compounds target LPS-MD2 binding or MD2-TLR4 binding. Biologicals based on MD2 have not been studied. Previous studies showed that antagonists to $\alpha v\beta 3$ block TLR4 signaling from LPS, and that integrin $\alpha v\beta 3$ is associated with the LPS/MD2/TLR4 complex. However, the specifics of the role of integrin $\alpha v\beta 3$ are unclear. To identify the role of integrin $\alpha v\beta 3$ in MD2-TLR4 signaling, docking simulation of interaction between integrin $\alpha v\beta 3$ and MD2 was performed. The simulation predicted that MD2 directly binds to integrin $\alpha v\beta 3$ without steric hindrance between TLR4 and $\alpha v\beta 3$ indicating that $\alpha v\beta 3$ MD2, and TLR4 can stay together, making ternary complex. It was discovered that $\alpha v\beta 3$ directly binds to MD2 in ELISA-type binding assays, and the integrin-binding sites in MD2 were identified by introducing point mutations in the potential integrin-binding site in MD2. The integrin-binding site in MD2 does not overlap with that of TLR4-binding site in MD2, consistent with the prediction. Such MD2 mutants should have specificity and affinity comparable to that of WT MD2, and are defective in signaling functions. Such MD2 mutants are studied as antagonists for LPS/TLR4 signaling in vitro and in animal models of sepsis.

This study identifies the role of integrin $\alpha v\beta 3$ in LPS/MD2/TLR4 signaling using MD2 mutants as tools. Further, this study helps develop potential antagonists for this signaling pathways from MD2 mutants defective in integrin binding.

MD2 Mutants Defective in Integrin Binding as Antagonists In Vitro and In Vivo First, the ability of human MD2 mutants are studied as a dominant negative antagonist to attenuate LPS/TLR4/MD2 signaling in monocytes and in HEK293 NF-kB reporter cells that express TLR4/MD2/CD14.

Second, the ability of human MD2 mutants to suppress LPS/TLR4 signaling are studied in a sepsis model using humanized TLR4/MD2 transgenic mice.

SIGNIFICANCE

Toll-like receptors (TLRs) recognize pathogen-associated molecular patterns (PAMPs) and activate downstream transcription factors to produce various pro-inflammatory cytokines and clear invading pathogens (Akira and Takeda 2004). Among TLRs, Toll-like receptor 4 (TLR4) was discovered as a sensing receptor for bacterial lipopolysaccharide (LPS) (Beutler 2000). Membrane bound TLR4 recognizes LPS and signals with enhanced efficiency after forming a receptor complex with accessory proteins including myeloid differentiation protein 2 (MD2), 1,PS binding protein, and CD14 (Jiang et al. 2005, Kobayashi et al. 2006. Park et al. 2009). Docking the LPS-CD14 complex onto the TLR4-MD2 complex initiates signaling through both the myeloid differentiation primary response 88 (MyD88) and Toll-IL-1 receptor-domain-containing adapter-inducing interferon-μ (TRIF) pathways (Peng et al. 2015). MyD88-dependent signaling activates nuclear factor-κB (NF-κB) and leads to the production of pro-inflammatory cytokines such as IL-6, tumor necrosis factor α (TNF-α) and IL-12. Since TLR4 plays a critical role in the development of cancer, inhibition of LPS-induced TLR4 signaling is valuable for the prevention and treatment of cancer as well.

MD2 binds bacterial lipopolysaccharide (LPS) (Kim et at. 2007, Ohto et al. 2007). MD2 cooperates with TLR4 in the innate immune response to bacterial lipopolysaccharide (LPS), and with TLR2 in the response to cell wall components from Gram-positive and Gram-negative bacteria (Dziarski et al. 2001, Visintin et at. 2001). MD2 enhances TLR4-dependent activation of NF-kappa-B (Shimazu et al. 1999). Cells expressing both MD2 and TLR4, but not TLR4 alone, respond to LPS (Shimazu et al. 1999). MD2 is thus essential for correct intracellular distribution and LPS recognition of TLR4, and MD2 knockout mice do not respond to LPS and survive endotoxic shock (Nagai et al. 2002).

Several inhibitors for the TLR4/MD2 complex have been developed. Eritoran (also known as E5564), second-generation lipid A analog, competes with LPS for the same hydrophobic binding pocket of MD2 and induces a different conformational change to reduce the stability of TLR4-MD2 complex and inhibits TLR4 signaling (Visintin et al. 2005). But it did not reduce mortality in patients with severe sepsis in phase III clinical trials (Opal et al. 2013). Clinical trials of the TLR4 inhibitor, TAK-242 (Takeda Pharmaceutical), also failed as it did not suppress the cytokine surge in patients with severe sepsis and related respiratory or cardiovascular disease (Rice et al. 2010). A small compound that binds to MD2 and blocks MD2-TLR4 interaction has been discovered but not tested in clinical trials. Therefore, new effective antagonists are needed to be discovered. Biologicals based on MD2 have not been previously studied.

Integrins are known to directly interact with many other small ligands including growth factors and cytokines. Integrins are a family of cell adhesion receptors that recognize ECM (extracellular matrix, such as fibronectin and collagen) and cell surface ligands (e.g., ICAM-1 and VCAM-1) (Hynes 2002). Integrins are transmembrane αvβ3 heterodimers, with 18 a and 8l3 subunits having been identified (Takada et al. 2007). Earlier studies identified many growth factors and cytokines (total 18) as new integrin ligands using virtual screening of protein data bank. These studies resulted in the model, in which integrins bind to ligands (e.g., FGF and IGF) and play a role in important biological processes (e.g., growth factor signaling) by inducing integrin-growth factor complex on the cell surface (ternary complex model) (Mori and Takada 2013, Takada et al. 2017). Interestingly, growth factor mutants defective in integrin binding were defective in signaling functions and ternary complex formation, and act as antagonists of growth factor signaling (dominant-negative effects) and suppressed tumor growth or inflammation in vivo (growth factor decoys).

It was also showed that IL-1β directly binds to integrin αvβ3 and that this process is required for IL-1β signaling (NF-kB activation) (Takada et al. 2017). IL-1β mutants defective in integrin binding were generated by mutating the Lys residues exposed to the surface. These mutants were defective in NF-kB activation, although they still bind to IL-1 receptor (Takada et al. 2017). Since signaling pathways for IL-1β and TLR4 are almost identical, it is speculated that integrins may be involved in TLR4 signaling.

Integrin αvβ3 Involvement in TLR4 Signaling

It has been reported that integrin αvβ3 is required for LPS-induced TLR4/TLR2-mediated activation of human monocytes (Gerold et al. 2008, Opal et al. 2013). Furthermore, monocytes from patients with Glanzmann thrombasthenia, which lack integrin αvβ3, were completely unresponsive to LPS. In addition, integrin αvβ3 forms a complex with TLR4 and this complex dissociated after LPS stimulation. Consistently, antagonists to integrin αvβ3 (e.g., snake venom disintegrin) (Hsu et al. 2016) were shown to enhance survival from sepsis in animal models. Furthermore, αvβ3 has been shown to associate with the TLR4-MD2-LPS complex and makes ternary complex (integrin αvβ3-MD2-TKR4 complex) (Hsu et al. 2016). It is unclear, however, how integrin αvβ3 interacts with the TLR4-MD2 complex. Preliminary, studies showed that MD2 directly hound to integrin αvβ3 and identified MD2 mutants defective in integrin binding by introducing point mutations in the predicted integrin-binding site in MD2.

Role of Soluble MD-2 in Sepsis

Previous studies showed that plasma from patients with severe sepsis and septic shock but not normal plasma supports LPS activation of epithelial cells expressing TLR4. High-level soluble MD-2 was found in urine from a patient with septic shock and in lung edema fluids from patients with adult respiratory distress syndrome (ARDS) (Pugin et al. 2004). These results suggest that septic plasma containing soluble MD-2 leaking into the extravascular space supports LPS activation of TLR4-expressing epithelial cells. Therefore, soluble MD-2 is an important mediator of organ inflammation during sepsis.

Antagonistic MD2 mutants in in vitro and in vivo models of sepsis

Antagonistic MD-2 mutants are able to suppress organ inflammation during sepsis. This study investigates the role of integrins in TLR4/MD2 signaling and develops MD2 mutants that act as antagonists for TLR4 signaling. Despite that the role of integrins in TLR4 has not been fully established by structural biology and it is unclear if integrin binding to MD2 induces integrin-MD2-TLR4 complex yet, preliminary studies showed direct binding of integrins to MD2 in a cation-dependent manner and produced MD2 mutants defective in integrin binding.

SUMMARY OF DISCOVERY

MD2 has been discovered as a ligand of integrin αvβ3 by docking simulation and mutagenesis studies. Potential integrin-binding site has been identified in MD2 protein. This study shows that integrin-binding defective MD2 is defective in TLR4 signaling and acts as antagonist for TLR4 signaling.

MD2 Mutants Defective in Integrin Binding as Potential Antagonists

Preliminary studies: wild-type MD2 (with 6×His tag (SEQ ID NO: 2)) was generated in bacteria using PET28 vector and purified using Ni-NTA affinity chromatography. Preliminary studies found that integrin αvβ3 directly binds to MD2 in ELISA-type binding assays (FIG. 2*a*). The MD2 protein bound to soluble integrin αvβ3 in a cation-dependent manner (FIG. 2*b*) and this interaction was blocked by heating (80° C. for 10 min), indicating that MD2 is an integrin ligand and requires proper folding for interaction. Recombinant soluble integrin αvβ3 was produced in HEK293 cells and purified by Ni-NTA affinity chromatography (Takagi et al. 2001). Soluble integrins also commercially available (e.g., R&D.inc). The 3D structure of the integrin-MD2-TLR4 complex will be determined.

Docking simulation of interaction between integrin αvβ3 and MD2 was performed. This study indicates that integrin αvβ3 and TLR4 simultaneously bind to MD2 (the TLR4-binding site and the predicted integrin-binding site are distinct). The simulation shows the positions of αvβ3-binding site in MD2 (FIG. 1*b*). Mutations were introduced in the predicted integrin-binding interface of MD2. The ability of the MD2 mutants in ELISA-type binding assays was measured using soluble αvβ3 (FIG. 2*c*). It was discovered that Lys20 and Lys39 significantly reduced the integrin binding. These findings indicate that Lys20 and Lys39 are critically involved in integrin binding. If integrin αvβ3 binding to MD2 is required for TLR4 signaling as previous studies suggested (Hsu et al. 2016), then MD2 mutants defective in integrin binding will be defective in inducing TLR4 signaling and can act as a dominant-negative antagonist (MD2 decoy).

It has been reported that a natural mutation in MD-2 (Thr35 to Ala), which is close to Lys20 and Lys39, markedly reduced the ability of MD-2 to induce signals from LPS (Hamann et al. 2004). It is possible that Thr35 to Ala mutation affects integrin binding to MD-2. There are two glycosylation sites (Asn26 and Asn114) and it is not likely that glycosylation blocks the access of integrins to MD2 (FIG. 1*b*).

The ability of MD-2 (WT and mutants) to induce NF-kB activation are measured using HEK293 cells that express NF-kB SEAP reporter and TLR-4. TLR-4 YFP expression plasmid will be transiently transfected and LPS (10 ng/ml) and soluble MD2. IL-1β (10 ng/ml) will be used as a positive control. Mutant MD-2 defective in integrin binding is defective in signaling functions (e.g., NF-kB activation) and suppress NF-kB activation induced by WT MD2. This is based on previous studies that direct binding to integrin $\alpha v\beta 3$ to TLR4/MD2 complex is critically required for TLR4 signaling from bacterial LPS (see introduction).

The present study showed that integrin $\alpha v\beta 3$ binds to MD2. It is believed that integrin $\alpha v\beta 3$-MD2-TLR4 ternary complex formation is required. Thus, MD2 mutants defective in integrin binding act as dominant-negative antagonists and these MD-2 mutants act as antagonists (MD2 decoys).

Since MD2 decoys have potential as therapeutics in TLR4-positive cancer and sepsis, MD2 decoys are tested for their effectiveness in suppressing TLR4 signaling during sepsis in animal sepsis models.

METHODS a) In Vitro Study

NF-kB reporter assays. HEK293 cells do not express TLR-4 or MD-2. HEK293 cells are transfected with human TLR-4 and NF-kB reporter (secreting embryonic alkaline phosphatase, SEAP) gene, CD14 and MD2 (HEK-blue-HTLR4, available from Invitrogen). The functions of MD2 mutants are measured using this reporter cells for their blocking of LPS-mediated TLR signaling (NF-kB activation). Cells are then incubated with MD2 mutants and 10 ng/ml LPS. SEAP secreted in the culture medium is measured.

Effect of MD2 mutants in human peripheral monocytes. MD2 mutants are tested for their suppression of LPS/TLR4 signaling in human monocytes. Monocytes are cultured in the presence of MD2 mutants and control vehicle and cells will be harvested.

Real-time quantitative PCR assay to evaluate inflammatory cytokine expression. Total RNA is isolated from cells using TRIZOL. Reverse transcription and quantitative PCR (RT-qPCR) is performed using RT-qPCR Kit (Invitrogen). Real-time quantitative PCR is carried out. Primers of genes including TNF-α, IL-6, IL-1β, IL-12, IL-10, COX-2 and β-actin are synthesized. The relative amount of each gene is normalized to the amount of (β-actin.

Cytokine measurement by Luminex assay to evaluate inflammatory cytokine production blockage from monocytes. Monocytes are stimulated with LPS in the presence of various doses of MD2 antagonists. Cytokine concentration in the supernatant is measured by Luminex multiplex assay using a human inflammatory cytokine panel.

WT human MD2 suppresses the sensitivity of monocytes to LPS, but MDS mutants do not. The amount of MD2 mutants required for effective suppression of LPS/TLR4 signaling in vitro is determined.

MD2 (WT and mutants) that were synthesized in *E. coli* (as in the preliminary studies) are first used. Then MD2 proteins that are expressed in mammalian cells using mammalian expression vector (e.g., pCDNA3.1) are used.

b) In Vivo Study

Due to consideration relating to species specificity in MD2/TLR4 interactions, humanized MD2/TLR4 mice (#031051, B6.Cg-Tg(LY96)7020Haj Tg(TLR4)5271Haj/J, Jackson laboratory) are used for in vivo study. These mice are first cryo preserved and recovered within 10-14 weeks. It has been reported that MD2 is an important mediator of multiple organ inflammation during sepsis (Pugin et al. 2004). Plasma from septic patients contains soluble MD2 leaking into the extravascular space, which supports LPS activation of epithelial cells that express TLR4 but not MD2. Plasma from healthy persons does not contain MD2 (Pugin et al. 2004). Therefore, soluble recombinant antagonistic MD2 (decoys) suppresses organ inflammation by blocking the binding of MD2 in septic plasma to TLR4 when MD2 decoys are administered (intravenously or intraperitoneally).

LPS-induced septic mortality in humanized MD2/TLR4 mice: Male humanized MD2/TLR4_C57BL/6 mice (#031051, B6.Cg-Tg(LY96)7020Haj Tg(TLR4)5271Haj/J, Jackson laboratory) weighing 18-22 g will be randomly divided into four groups (n=10 per group). Mice are injected with 200 μl of LPS (at 20 mg per kg in 0.9% saline, i.v. through the tail vein) 15 min before (for treatment) or after (for prevention) an injection of recombinant human MD2 mutants (i. v. through the tail vein) respectively. Mice in both vehicle control group and LPS alone group received 100 μL of vehicle, and mice in the vehicle control group also received 200 μl of saline. After the LPS injection, body weight change and mortality will be recorded for 7 days.

LPS-induced inflammatory responses in humanized MD2/TLR4 mice: Male humanized MD2/TLR4 C57BL/6 mice weighing 18-22 g are randomly divided into six groups (n=10 per group). Mice in the LPS+recombinant MD2 mutants group are injected with 200 μl of LPS (at 20 mg per kg, i. v. through the tail vein) 15 min after being injected with recombinant MD2 mutants (i. v. through the tail vein). Mice in both vehicle control group and LPS alone group receive 100 μl of vehicle, and mice in the vehicle control group also receive 200 μl of saline. Two or eight hours after the LPS injection, the mice are anaesthetized and killed. The blood samples are collected from the right ventricle using a heparin containing syringe with a needle. The serum TNF-α and IL-6 levels are determined using ELISA. Both lung and liver are harvested for evaluation of histopathology and inflammatory gene expression by qRT-PCR. Liver tissues will be homogenized for RNA extraction and real-time qPCR analysis as described above.

Serum cytokine levels are suppressed by MD2 mutants. The amount of MD2 mutants required for effectively suppressing cytokine production is determined. Recombinant human MD2 mutants suppress LPS/TLR4 signaling in vivo resulting in reduced gene expression in inflammatory NFkB pathway. Reduced pathology is evident with reduced lymphocyte infiltration by H&E staining in lung and liver. Plasma MD2 levels are increased in septic patients (not detected in healthy controls) (Pugin et al. 2004). MD2 mutants can suppress LPS/TLR4 signaling by competing with endogenous WT MD2.

Statistical analysis and power analysis: Tumor growth curves are compared across groups using standard repeated measures mixed models (Laird and Ware 1982). These models allow for possibly unequal spacing of measurements or unequal lengths of follow-up, as for example, if some mice develop unsustainable tumor burdens and are sacrificed early. These models are formulated first to test specifically for MD2 mutant-treated mice vs. control, and then to test for the added impact of increasing doses, to identify an optimal dose level, on LPS/TLR4 signaling and survival.

Results: TLR4 signaling is a major therapeutic target for sepsis, but biologicals based on MD2 have not been studied as a target for drug discovery. This is because the direct binding of integrin αvβ3 to MD2 was not established previously. It has been discovered that αvβ3 directly binds to MD2, which results in integrin αvβ3-MD2-TLR4 ternary complex formation. This is consistent with previous reports that integrin αvβ3 and TLR4 are associated, and that antagonists to αvβ3 blocked LPS signaling (see introduction).

αvβ3-MD2 interaction is a novel target for drug discovery. This study establishes that MD2 mutants defective in integrin binding are defective in TLR4 signaling and act as antagonists to TLR4 signaling in vitro and in vivo.

When MD2 is synthesized in LPS-negative *E. coli*, it is possible that MD2 without N-glycosylation may not induce signals properly. When MD2 proteins (WT and mutants) are synthesized in mammalian cells (e.g., HEK293 cells), this potential concern is addressed.

All patents, patent applications, and other publications, including GenBank Accession Numbers, cited in this application are incorporated by reference in the entirety for all purposes.

---

INFORMAL SEQUENCE LISTING

SEQ ID NO: 1 MD2 amino acid sequence
MLPFLFFSTLFSSIFTEAQKQYWVCNSSDASISYTYCDKMQYPISINVN
PCIELKRSKGLLHIFYIPRRDLKQLYFNLYITVNTMNLPKRKEVICRGS
DDDYSFCRALKGETVNTTISFSFKGIKFSKGKYKCVVEAISGSPEEMLF
CLEFVILHQPNSN

---

REFERENCES

Akira, S. and K. Takeda (2004). "Toll-like receptor signalling." *Nat Rev Immunol* 4(7): 499-511. 10.1038/nri1391

Beutler, B. (2000). "Tlr4: central component of the sole mammalian LPS sensor." *Curr Opin Immunol* 12(1): 20-26.

Dziarski, R., Q. Wang, K. Miyake, C. J. Kirschning and D. Gupta (2001). "MD-2 enables Toll-like receptor 2 (TLR2)-mediated responses to lipopolysaccharide and enhances TLR2-mediated responses to Gram-positive and Gram-negative bacteria and their cell wall components." *J Immunol* 166(3): 1938-1944. 10.4049/jimmunol.166.3.1938

Gerold, G., K. Abu Ajaj, M. Bienert, H. J. Laws, A. Zychlinsky and J. L. de Diego (2008). "A Toll-like receptor 2-integrin beta3 complex senses bacterial lipopeptides via vitronectin." *Nat Immunol* 9(7): 761-768. 10.1038/ni.1618

Hamann, L., 0. Kumpf, M. Muller, A. Visintin, J. Eckert, P. M. Schlag and R. R. Schumann (2004). "A coding mutation within the first exon of the human MD-2 gene results in decreased lipopolysaccharide-induced signaling." *Genes Immun* 5(4): 283-288. 10.1038/sj.gene.6364068

Hsu, C. C., W. J. Chuang, C. H. Chung, C. H. Chang, H. C. Peng and T. F. Huang (2016). "Snake Venom Disintegrin Inhibits the Activation of Toll-Like Receptors and Alleviates Sepsis through Integrin alphaVbeta3 Blockade." *Sci Rep* 6: 23387. 10.1038/srep23387 PMC4796821

Hynes, R. O. (2002). "Integrins: bidirectional, allosteric signaling machines." *Cell* 110(6): 673-687.

Jiang, Z., P. Georgel, X. Du, L. Shamel, S. Sovath, S. Mudd, M. Huber, C. Kalis, S. Keck, C. Galanos, M. Freudenberg and B. Beutler (2005). "CD14 is required for MyD88-independent LPS signaling." *Nat Immunol* 6(6): 565-570. 10.1038/ni1207

Kim, H. M., B. S. Park, J. I. Kim, S. E. Kim, J. Lee, S. C. Oh, P. Enkhbayar, N. Matsushima, H. Lee, 0. J. Yoo and J. O. Lee (2007). "Crystal structure of the TLR4-MD-2 complex with bound endotoxin antagonist Eritoran." *Cell* 130(5): 906-917. 10.1016/j.cell.2007.08.002

Kobayashi, M., S. Saitoh, N. Tanimura, K. Takahashi, K. Kawasaki, M. Nishijima, Y. Fujimoto, K. Fukase, S. Akashi-Takamura and K. Miyake (2006). "Regulatory roles for MD-2 and TLR4 in ligand-induced receptor clustering." *J Immunol* 176(10): 6211-6218.

Laird, N. M. and J. H. Ware (1982). "Random-effects models for longitudinal data." *Biometrics* 38(4): 963-974.

Mori, S. and Y. Takada (2013). "Crosstalk between Fibroblast Growth Factor (FGF) Receptor and Integrin through Direct Integrin Binding to FGF and Resulting Integrin-FGF-FGFR Ternary Complex Formation." *Medical Sciences* 1(1): 20-36. 10.3390/medsci1010020

Nagai, Y., S. Akashi, M. Nagafuku, M. Ogata, Y. Iwakura, S. Akira, T. Kitamura, A. Kosugi, M. Kimoto and K. Miyake (2002). "Essential role of MD-2 in LPS responsiveness and TLR4 distribution." *Nat Immunol* 3(7): 667-672. 10.1038/ni809

Ohto, U., K. Fukase, K. Miyake and Y. Satow (2007). "Crystal structures of human MD-2 and its complex with antiendotoxic lipid IVa." *Science* 316(5831): 1632-1634. 10.1126/science.1139111

Opal, S. M., P. F. Laterre, B. Francois, S. P. LaRosa, D. C. Angus, J. P. Mira, X. Wittebole, T. Dugernier, D. Perrotin, M. Tidswell, L. Jauregui, K. Krell, J. Pachl, T. Takahashi, C. Peckelsen, E. Cordasco, C. S. Chang, S. Oeyen, N. Aikawa, T. Maruyama, R. Schein, A. C. Kalil, M. Van Nuffelen, M. Lynn, D. P. Rossignol, J. Gogate, M. B. Roberts, J. L. Wheeler, J. L. Vincent and A. S. Group (2013). "Effect of eritoran, an antagonist of MD2-TLR4, on mortality in patients with severe sepsis: the ACCESS randomized trial." *JAMA* 309(11): 1154-1162. 10.1001/jama.2013.2194

Park, B. S., D. H. Song, H. M. Kim, B. S. Choi, H. Lee and J. O. Lee (2009). "The structural basis of lipopolysaccharide recognition by the TLR4-MD-2 complex." *Nature* 458(7242): 1191-1195. 10.1038/nature07830

Peng, J., X. Tao, R. Li, J. Hu, J. Ruan, R. Wang, M. Yang, R. Yang, X. Dong, S. Chen, A. Xu and S. Yuan (2015). "Novel Toll/IL-1 Receptor Homologous Region Adaptors Act as Negative Regulators in Amphioxus TLR Signaling." *J Immunol* 195(7): 3110-3118. 10.4049/jimmunol.1403003

Pugin, J., S. Stern-Voeffray, B. Daubeuf, M. A. Matthay, G. Elson and I. Dunn-Siegrist (2004). "Soluble MD-2 activity in plasma from patients with severe sepsis and septic shock." *Blood* 104(13): 4071-4079. 10.1182/blood-2003-04-1290

Rice, T. W., A. P. Wheeler, G. R. Bernard, J. L. Vincent, D. C. Angus, N. Aikawa, I. Demeyer, S. Sainati, N. Amlot, C. Cao, M. Ii, H. Matsuda, K. Mouri and J. Cohen (2010). "A randomized, double-blind, placebo-controlled trial of TAK-242 for the treatment of severe sepsis." *Crit Care Med* 38(8): 1685-1694. 10.1097/CCM.0b013e3181e7c5c9

Shimazu, R., S. Akashi, H. Ogata, Y. Nagai, K. Fukudome, K. Miyake and M. Kimoto (1999). "MD-2, a molecule that confers lipopolysaccharide responsiveness on Toll-like receptor 4." *J Exp Med* 189(11): 1777-1782. 10.1084/jem.189.11.1777 PMC2193086

Takada, Y., K. Takada and M. Fujita (2017). "Crosstalk between insulin-like growth factor (IGF) receptor and integrins through direct integrin binding to IGF1." *Cytokine Growth Factor Rev* 34: 67-72. 10.1016/j.cytogfr.2017.01.003 PMC5401657

Takada, Y., X. Ye and S. Simon (2007). "The integrins." *Genome Biol* 8(5): 215. 10.1186/gb-2007-8-5-215 PMC1929136

Takada, Y. K., J. Yu, M. Fujita, J. Saegusa, C. Y. Wu and Y. Takada (2017). "Direct binding to integrins and loss of disulfide linkage in interleukin-lbeta (IL-lbeta) are involved in the agonistic action of IL-lbeta." *J Biol Chem* 292(49): 20067-20075. 10.1074/jbc.M117.818302 PMC5723996

Takagi, J., H. P. Erickson and T. A. Springer (2001). "C-terminal opening mimics 'inside-out' activation of integrin alpha5beta1." *Nat Struct Biol* 8(5): 412-416. 10.1038/87569 87569 [pii]

Visintin, A., K. A. Halmen, E. Latz, B. G. Monks and D. T. Golenbock (2005). "Pharmacological inhibition of endotoxin responses is achieved by targeting the TLR4 coreceptor, MD-2." *J Immunol* 175(10): 6465-6472.

Visintin, A., A. Mazzoni, J. A. Spitzer and D. M. Segal (2001). "Secreted MD-2 is a large polymeric protein that efficiently confers lipopolysaccharide sensitivity to Toll-like receptor 4." *Proc Natl Acad Sci USA* 98(21): 12156-12161. 10.1073/pnas.211445098 PMC59784

What is claimed is:

1. An isolated peptide comprising SEQ ID NO:1 with at least one substitution at residue 20 or 39, wherein the peptide has decreased binding to integrin αvβ3 compared with SEQ ID NO:1.

2. The peptide of claim 1, wherein the substitution is K20E or K39E.

3. The peptide of claim 1, wherein the substitution is not K20A or K39A.

4. The peptide of claim 1, wherein the peptide comprises SEQ ID NO:1 with K20E substitution.

5. The peptide of claim 1, wherein the peptide comprises SEQ ID NO: 1 with K39E substitution.

6. A nucleic acid comprising a polynucleotide sequence encoding the peptide of claim 1.

7. An expression cassette comprising a polynucleotide sequence encoding the peptide of claim 1 operably linked to a promoter.

8. A vector comprising the expression cassette of claim 7.

9. A host cell comprising the vector of claim 8.

10. A composition comprising (1) the peptide of claim 1, a nucleic acid comprising a polynucleotide sequence encoding the peptide, an expression cassette comprising the polynucleotide sequence, a vector comprising the expression cassette, or a host cell comprising the vector; and (2) a pharmaceutically acceptable excipient.

11. A method for suppressing inflammation, comprising administering to a subject in need thereof an effective amount of the composition of claim 10.

12. The method of claim 11, wherein the composition is administered to the subject by a route selected from the group consisting of intravenous, subcutaneous, intraperitoneal, intraosseous, intramuscular, and oral.

13. The method of claim 11, wherein the subject is suffering from or at risk of developing sepsis.

14. The method of claim 13, wherein one or more signs, symptoms, and/or sequelae associated with sepsis are mitigated in the subject.

15. A method for identifying an inhibitor of MD2-integrin αvβ3 binding, comprising the steps of (1) contacting integrin αvβ3 and a polypeptide, which consists of (i) the amino acid sequence of SEQ ID NO: 1 or (ii) the amino acid sequence of SEQ ID NO:1 and at least one heterologous amino acid sequence, in the presence of a test compound, under conditions permissible for MD2-integrin αvβ3 binding; and (2) detecting the level of polypeptide-integrin αvβ3 binding, wherein a decrease in the level of binding when compared with the level of binding in the absence of the test compound indicates the compound as an inhibitor of MD2-integrin αvβ3 binding.

16. The method of claim 15, wherein the polypeptide consists of the amino acid sequence of SEQ ID NO:1.

17. The method of claim 15, wherein the polypeptide consists of the amino acid sequence of SEQ ID NO:1 and a heterologous amino acid sequence.

18. The method of claim 17, wherein the heterologous amino acid sequence is 6×His.

19. The method of claim 15, wherein the integrin αvβ3 is expressed on a cell surface.

20. A kit for inhibiting inflammation, comprising a first container containing the composition of claim 10 and a second container containing a second therapeutic agent.

* * * * *

SEQUENCE LISTING

```
<160> NUMBER OF SEQ ID NOS: 3

<210> SEQ ID NO 1
<211> LENGTH: 160
<212> TYPE: PRT
<213> ORGANISM: Homo sapiens

<400> SEQUENCE: 1

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Arg Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: misc_feature
<222> LOCATION: (1)..(10)
<223> OTHER INFORMATION: This sequence may encompass 6-10 "His" residues
```

-continued

<400> SEQUENCE: 3

```
His His His His His His His His His His
1               5                   10
```